(12) United States Patent
Williams et al.

(10) Patent No.: US 11,642,203 B2
(45) Date of Patent: *May 9, 2023

(54) ORAL IRRIGATOR HANDLE WITH HOSE CONNECTOR FITTINGS

(71) Applicant: WATER PIK, INC., Fort Collins, CO (US)

(72) Inventors: Brian R. Williams, Fort Collins, CO (US); Jeremy Johnson, Longmont, CO (US); Leland C. Leber, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 142 days.

This patent is subject to a terminal disclaimer.

(21) Appl. No.: 17/016,490

(22) Filed: Sep. 10, 2020

(65) Prior Publication Data
US 2020/0405463 A1    Dec. 31, 2020

Related U.S. Application Data

(63) Continuation of application No. 15/415,836, filed on Jan. 25, 2017, now Pat. No. 10,835,356.
(Continued)

(51) Int. Cl.
*A61C 17/02* (2006.01)
*A61C 17/032* (2006.01)
(Continued)

(52) U.S. Cl.
CPC ........ *A61C 17/0202* (2013.01); *A61C 17/032* (2019.05); *A61M 39/1055* (2013.01);
(Continued)

(58) Field of Classification Search
CPC . A61C 17/14; A61C 17/0202; A61C 17/0214; A61C 17/02; A61C 17/024;
(Continued)

(56) References Cited

U.S. PATENT DOCUMENTS

| 555,588 A | 3/1896 | Spencer |
| 1,278,225 A | 9/1918 | Schamberg |

(Continued)

FOREIGN PATENT DOCUMENTS

| CA | 851479 | 9/1970 |
| CH | 569905 | 11/1975 |

(Continued)

OTHER PUBLICATIONS

US RE27,274 E, 01/1972, Mattingly (withdrawn)
(Continued)

*Primary Examiner* — Timothy A Stanis
*Assistant Examiner* — Matthew R Moon
(74) *Attorney, Agent, or Firm* — Dorsey & Whitney LLP

(57) ABSTRACT

An oral irrigator handle including a housing and a first fitting, the first fitting including a first fitting inlet in fluid communication with a handle inlet in fluid communication with a fluid source and a first fitting outlet in fluid communication with the first fitting inlet. The handle includes a seal positioned around the first fitting and between the first fitting inlet and the first fitting outlet. A second fitting includes a second fitting inlet in fluid communication with the first fitting outlet and a second fitting outlet in fluid communication with the second fitting inlet. A bottom portion of the second fitting seats on a portion of the first fitting so that the seal engages an interior surface of the second fitting, a flow passage is coupled to the second fitting and in fluid communication with the second fitting outlet.

20 Claims, 13 Drawing Sheets

Related U.S. Application Data

(60) Provisional application No. 62/416,926, filed on Nov. 3, 2016, provisional application No. 62/286,792, filed on Jan. 25, 2016, provisional application No. 62/286,925, filed on Jan. 25, 2016.

(51) Int. Cl.
*A61M 39/10* (2006.01)
*F16L 27/00* (2006.01)
*A61C 17/14* (2006.01)
*A61C 1/00* (2006.01)
*A61C 17/00* (2006.01)

(52) U.S. Cl.
CPC ............ *A61C 1/0061* (2013.01); *A61C 17/00* (2013.01); *A61C 17/14* (2013.01); *F16L 27/00* (2013.01)

(58) Field of Classification Search
CPC . A61C 17/028; A61C 17/032; A61C 7/00–06; A61C 1/0061; A61C 17/06–135; A61H 9/0021; A61H 9/0028; A61H 33/00; A61H 33/0087; A61H 33/028; F16L 27/00; A61M 39/1055; A61M 39/1011; A61M 2039/1027; A61M 2039/1033
See application file for complete search history.

(56) References Cited

U.S. PATENT DOCUMENTS

| | | |
|---|---|---|
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,124,747 A | 7/1938 | Pieper |
| 2,171,292 A | 8/1939 | Pieper |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,783,919 A | 3/1957 | Ansell |
| 2,794,437 A | 6/1957 | Tash |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,204 S | 11/1967 | St. Clair et al. |
| D209,395 S | 11/1967 | Gilbert |
| 3,357,599 A | 12/1967 | Douglas et al. |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,393,676 A | 7/1968 | Kummer et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,851,643 A | 12/1974 | Musy |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,912,125 A | 10/1975 | Acklin |
| 3,921,297 A | 11/1975 | Vit |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,015,336 A | 4/1977 | Johnson |
| 4,052,002 A | 10/1977 | Stouffer et al. |
| D246,667 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |

(56) References Cited

U.S. PATENT DOCUMENTS

| | | |
|---|---|---|
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,013,300 A | 5/1991 | Williams |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Handler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,086,788 A | 2/1992 | Bally et al. |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |

(56) References Cited

U.S. PATENT DOCUMENTS

| | | |
|---|---|---|
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| D354,559 S | 1/1995 | Knute |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| D370,125 S | 5/1996 | Craft et al. |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D376,893 S | 12/1996 | Gornet |
| D377,091 S | 12/1996 | Scott, Sr. |
| 5,613,259 A | 3/1997 | Craft et al. |
| 5,616,028 A | 4/1997 | Hafele et al. |
| 5,626,472 A | 5/1997 | Pennetta |
| 5,634,791 A | 6/1997 | Matsuura et al. |
| 5,636,904 A | 6/1997 | Bell et al. |
| 5,636,987 A | 6/1997 | Serfaty |
| 5,640,735 A | 6/1997 | Manning |
| D382,407 S | 8/1997 | Craft et al. |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| D389,091 S | 1/1998 | Dickinson |
| 5,709,545 A | 1/1998 | Johnston et al. |
| D390,934 S | 2/1998 | McKeone |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,471 A | 7/1998 | Tseng et al. |
| 5,779,654 A | 7/1998 | Foley et al. |
| 5,788,289 A | 8/1998 | Cronley |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,933,918 A | 8/1999 | Wallays |
| 5,934,902 A | 8/1999 | Abahusayn |
| D413,975 S | 9/1999 | Maeda |
| D416,999 S | 11/1999 | Miyamoto |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,047,429 A | 4/2000 | Wu |
| D424,181 S | 5/2000 | Caplow |
| D425,615 S | 5/2000 | Bachman et al. |
| D425,981 S | 5/2000 | Bachman et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,120,755 A | 9/2000 | Jacobs |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,238,211 B1 | 5/2001 | Esrock |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |
| D453,453 S | 2/2002 | Lun |

(56) References Cited

U.S. PATENT DOCUMENTS

| | | |
|---|---|---|
| D455,201 S | 4/2002 | Jones |
| D455,203 S | 4/2002 | Jones |
| 6,363,565 B1 | 4/2002 | Paffrath |
| D457,949 S | 5/2002 | Krug |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,558,344 B2 | 5/2003 | McKinnon et al. |
| 6,561,808 B2 | 5/2003 | Neuberger et al. |
| D475,346 S | 6/2003 | McCurrach et al. |
| D476,743 S | 7/2003 | D'Silva |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| 6,997,393 B1 | 2/2006 | Angold et al. |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| D538,474 S | 3/2007 | Sheppard et al. |
| 7,235,176 B1 | 6/2007 | Takagi et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D764,051 S | 8/2016 | Wang |
| D766,423 S | 9/2016 | Kim et al. |
| D772,396 S | 11/2016 | Kim et al. |
| D772,397 S | 11/2016 | Kim et al. |

(56) References Cited

U.S. PATENT DOCUMENTS

| | | | |
|---|---|---|---|
| D774,651 S | 12/2016 | Kaib | |
| D776,253 S | 1/2017 | Li | |
| D782,326 S | 3/2017 | Fath | |
| D782,656 S | 3/2017 | Au | |
| D786,422 S | 5/2017 | Au | |
| 10,779,922 B2 | 9/2020 | Wagner et al. | |
| 10,835,356 B2* | 11/2020 | Williams | A61C 17/032 |
| 2002/0090252 A1 | 7/2002 | Hall et al. | |
| 2002/0108193 A1 | 8/2002 | Gruber | |
| 2002/0119415 A1 | 8/2002 | Bailey | |
| 2002/0152565 A1 | 10/2002 | Klupt | |
| 2003/0060743 A1 | 3/2003 | Chang | |
| 2003/0098249 A1 | 5/2003 | Rollock | |
| 2003/0204155 A1 | 10/2003 | Egeresi | |
| 2003/0213075 A1 | 11/2003 | Hui et al. | |
| 2004/0045107 A1 | 3/2004 | Egeresi | |
| 2004/0076921 A1 | 4/2004 | Gofman et al. | |
| 2004/0122377 A1 | 6/2004 | Fischer et al. | |
| 2004/0126730 A1 | 7/2004 | Panagotacos | |
| 2004/0209222 A1 | 10/2004 | Snyder | |
| 2005/0049620 A1 | 3/2005 | Chang | |
| 2005/0064371 A1 | 3/2005 | Soukos et al. | |
| 2005/0101894 A1 | 5/2005 | Hippensteel | |
| 2005/0102773 A1 | 5/2005 | Obermann et al. | |
| 2005/0144745 A1 | 7/2005 | Russell | |
| 2005/0177079 A1 | 8/2005 | Pan | |
| 2005/0271531 A1 | 12/2005 | Brown et al. | |
| 2006/0008373 A1 | 1/2006 | Schutz | |
| 2006/0010624 A1 | 1/2006 | Cleland | |
| 2006/0026784 A1 | 2/2006 | Moskovich et al. | |
| 2006/0057539 A1 | 3/2006 | Sodo | |
| 2006/0078844 A1 | 4/2006 | Goldman et al. | |
| 2006/0079818 A1 | 4/2006 | Yande | |
| 2007/0077810 A1 | 4/2007 | Gogel et al. | |
| 2007/0082316 A1 | 4/2007 | Zhadanov et al. | |
| 2007/0082317 A1 | 4/2007 | Chuang | |
| 2007/0113360 A1 | 5/2007 | Tsai | |
| 2007/0199616 A1 | 8/2007 | Chotenovsky | |
| 2007/0202459 A1 | 8/2007 | Boyd et al. | |
| 2007/0203439 A1 | 8/2007 | Boyd et al. | |
| 2007/0254260 A1 | 11/2007 | Alden | |
| 2008/0189951 A1 | 8/2008 | Molema et al. | |
| 2008/0213719 A1 | 9/2008 | Giniger et al. | |
| 2009/0061384 A1* | 3/2009 | Thomssen | A61C 1/08 433/132 |
| 2009/0070949 A1 | 3/2009 | Sagel et al. | |
| 2009/0082706 A1 | 3/2009 | Shaw | |
| 2009/0124945 A1 | 5/2009 | Reich et al. | |
| 2009/0163839 A1 | 6/2009 | Alexander | |
| 2009/0188780 A1 | 7/2009 | Watanabe | |
| 2009/0281454 A1 | 11/2009 | Baker et al. | |
| 2010/0010524 A1 | 1/2010 | Barrington | |
| 2010/0015566 A1 | 1/2010 | Shaw | |
| 2010/0190132 A1 | 7/2010 | Taylor et al. | |
| 2010/0239998 A1 | 9/2010 | Snyder et al. | |
| 2010/0261134 A1 | 10/2010 | Boyd et al. | |
| 2010/0261137 A1 | 10/2010 | Boyd et al. | |
| 2010/0326536 A1 | 12/2010 | Nan | |
| 2010/0330527 A1 | 12/2010 | Boyd et al. | |
| 2011/0027749 A1 | 2/2011 | Syed | |
| 2011/0076090 A1 | 3/2011 | Wu et al. | |
| 2011/0097683 A1 | 4/2011 | Boyd et al. | |
| 2011/0139826 A1 | 6/2011 | Hair et al. | |
| 2011/0144588 A1 | 6/2011 | Taylor et al. | |
| 2011/0184341 A1 | 7/2011 | Baker et al. | |
| 2011/0307039 A1 | 12/2011 | Cornell | |
| 2012/0021374 A1 | 1/2012 | Cacka et al. | |
| 2012/0045730 A1 | 2/2012 | Snyder et al. | |
| 2012/0064480 A1 | 3/2012 | Hegemann | |
| 2012/0077145 A1 | 3/2012 | Tsurukawa | |
| 2012/0141952 A1 | 6/2012 | Snyder et al. | |
| 2012/0179118 A1 | 7/2012 | Hair | |
| 2012/0189976 A1 | 7/2012 | McDonough et al. | |
| 2012/0266396 A1 | 10/2012 | Leung | |
| 2012/0277677 A1 | 11/2012 | Taylor et al. | |
| 2012/0277678 A1 | 11/2012 | Taylor et al. | |
| 2012/0279002 A1 | 11/2012 | Sokol et al. | |
| 2012/0295220 A1 | 11/2012 | Thomas et al. | |
| 2013/0140382 A1* | 6/2013 | Eley | B05B 15/652 239/526 |
| 2013/0295520 A1 | 11/2013 | Hsieh | |
| 2014/0106296 A1 | 4/2014 | Woodard et al. | |
| 2014/0116261 A1 | 5/2014 | Chen et al. | |
| 2014/0193774 A1 | 7/2014 | Snyder et al. | |
| 2014/0259474 A1 | 9/2014 | Sokol et al. | |
| 2014/0272769 A1 | 9/2014 | Luettgen et al. | |
| 2014/0272782 A1 | 9/2014 | Luettgen et al. | |
| 2014/0352088 A1 | 12/2014 | Wu | |
| 2014/0356810 A1 | 12/2014 | Novak | |
| 2015/0004559 A1 | 1/2015 | Luettgen et al. | |
| 2015/0147717 A1 | 5/2015 | Taylor et al. | |
| 2015/0173850 A1 | 6/2015 | Garrigues et al. | |
| 2015/0182319 A1 | 7/2015 | Wagner et al. | |
| 2016/0100921 A1 | 4/2016 | Ungar | |
| 2016/0151133 A1 | 6/2016 | Luettgen et al. | |
| 2017/0114495 A1* | 4/2017 | Date | D06F 87/00 |
| 2017/0209234 A1 | 7/2017 | Senff et al. | |

FOREIGN PATENT DOCUMENTS

| | | |
|---|---|---|
| CH | 655237 | 4/1986 |
| CH | 666807 | 8/1986 |
| CN | 87103004 | 12/1987 |
| CN | 2149184 | 12/1993 |
| CN | 2524708 | 12/2002 |
| CN | 2536202 | 2/2003 |
| CN | 201231191 | 5/2009 |
| CN | 100591625 | 2/2010 |
| CN | 201691300 | 1/2011 |
| CN | 201754925 | 3/2011 |
| CN | 204049908 | 12/2014 |
| CN | 108778182 | 11/2018 |
| DE | 1059879 | 6/1959 |
| DE | 1466963 | 5/1969 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| DE | 3101941 | 8/1982 |
| EP | 0023672 | 7/1980 |
| EP | 0229207 | 7/1987 |
| EP | 0515983 | 2/1992 |
| EP | 3554420 | 5/2021 |
| ES | 460563 | 5/1978 |
| FR | 2556954 | 6/1985 |
| FR | 2654627 | 5/1991 |
| GB | 472053 | 9/1937 |
| GB | 838564 | 6/1960 |
| GB | 1182031 | 2/1970 |
| GB | 1456322 | 11/1976 |
| GB | 2018605 | 10/1979 |
| JP | 55086451 | 6/1980 |
| JP | 55148553 | 11/1980 |
| JP | 56090220 | 7/1981 |
| JP | S56-115927 | 9/1981 |
| JP | 2-134150 | 5/1990 |
| JP | 06035569 | 2/1994 |
| JP | 10094747 | 4/1998 |
| JP | 2002532148 | 10/2002 |
| JP | 3140756 | 3/2008 |
| JP | 2009-39455 | 2/2009 |
| JP | 6694965 | 5/2020 |
| JP | 6889310 | 5/2021 |
| KR | 20100028231 | 3/2010 |
| KR | 20100029231 | 3/2010 |
| KR | 20120126265 | 11/2012 |
| KR | 102072661 | 2/2020 |
| WO | WO95/016404 | 6/1995 |
| WO | WO00/35403 | 6/2000 |
| WO | WO01/10327 | 2/2001 |
| WO | WO01/45631 | 6/2001 |
| WO | WO04/021958 | 3/2004 |
| WO | WO04/039205 | 5/2004 |

(56) References Cited

FOREIGN PATENT DOCUMENTS

| WO | WO2004/060259 | 7/2004 |
|---|---|---|
| WO | WO2004/062518 | 7/2004 |
| WO | WO2008/070730 | 6/2008 |
| WO | WO2008/157585 | 12/2008 |
| WO | WO2013/124691 | 8/2013 |

OTHER PUBLICATIONS

The Right Tool, Electron Fusion Devices, Inc., 2 pages, at least as early as Feb. 1991.
Japanese Packaging, 2 pages, at least as early as Dec. 2002.
Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: Woog International, "Products at a Glance: Home Dental Care System" Woog Orajet, 3 pages, at least as early as Dec. 18, 1998.
Website: http://www.just4teeth.com/product/Panasonic/Panasonic_Portable_Irrigator.htm, 2 pages, at least as early as Jun. 20, 2003.
Website: http://www.videodirectstore.com/store/merchant.mv?Screen=PROD&Product_Code=EW1'. . ., 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, dated Jul. 5, 2007.
European Search Report, EPO Application No. 07252693.2, 14 pages, dated Apr. 28, 2008.
European Examination Report, EPO Application No. 07250799.9, dated Feb. 5, 2009.
International Search Report, Application No. PCT/US2010/028180, 2 pages, dated May 18, 2010.
International Search Report, PCT/US2010/060800, 2 pages, dated Feb. 11, 2011.
International Search Report, PCT/US2011/052795, 10 pages, dated Jan. 17, 2012.
Waterpik SinuSense Website: http://www.insightsbyapril.com/2012/03/waterpik-natural-remedy-for-sinus.html, 8 pages, retrieved on May 31, 2012.
Website: https://www.waterpik.com/about-us/, 3 pages.
Waterpik WP350W Oral Irrigator. Dentist.net. Copyright date 2013. Date accessed: Mar. 30, 2017, 2 pages <http://www.dentalhoo.com/waterpik-wp350.asp>.
IPik Portable Oral Irrigator. AliExpress. Date reviewed: Oct. 5, 2016. <https://www.aliexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-yfAeyJa>, 18 pages.
Brite Leafs Professional Portable 2-in-1 Nasal Sinus & Oral Irrigator. Brite Leafs. Copyright date 2012, <http://www.briteleafs.com/product6.html> , 1 page.
AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.
U.S. Appl. No. 15/415,836, filed Jan. 25, 2017.

* cited by examiner

ORAL IRRIGATOR HANDLE WITH HOSE CONNECTOR FITTINGS

CROSS-REFERENCE TO RELATED APPLICATIONS

This application is a continuation application of U.S. non-provisional application Ser. No. 15/415,836 filed on Jan. 25, 2017 entitled "Swivel assembly for oral irrigator handle," which claims priority to U.S. provisional application No. 62/286,792 filed on 25 Jan. 2016 entitled "Swivel Assembly for Oral Irrigator Handle," U.S. provisional application 62/286,925 filed on 25 Jan. 2016 entitled "Reduced Form Factor Oral Irrigator," and U.S. provisional application No. 62/416,926 filed on 3 Nov. 2016 entitled "Reduced Form Factor Oral Irrigator," each of which is incorporated by reference herein in its entirety.

TECHNICAL FIELD

The present disclosure relates to health and personal hygiene equipment and more particularly, to oral irrigators.

BACKGROUND

Oral irrigators are typically used to clean a user's teeth and gums by discharging a pressurized fluid stream into a user's oral cavity. The fluid impacts the teeth and gums to remove debris. Often, the oral irrigator includes a fluid supply, such as a reservoir, that is fluidly connected by a pump to an oral irrigator tip, often through a handle. To direct the fluid in a desired direction, as well as to hold the handle in a comfortable position, a user often rotates either the handle or the tip relative to the handle. However, with countertop units, a hose fluidly connecting the handle to the reservoir can become tangled, or wrapped up as the user moves the handle around to different locations and orientations with respect to the base unit. This can make it difficult for the user to use the oral irrigator as the tangles can reduce the effective length of the hose, as well as make it difficult to store the handle back in the counter top unit (e.g., in a cradle).

The information included in this Background section of the specification, including any references cited herein and any description or discussion thereof, is included for technical reference purposes only and is not to be regarded subject matter by which the scope of the invention as defined in the claims is to be bound.

SUMMARY

In one exemplary implementation, the disclosure includes an oral irrigator handle. The handle includes, a handle housing; a tip for directing a focused stream of fluid connected to a first end of the handle connected to the tip, a swivel assembly received within the handle housing between the first end and a second end of the housing and fluidly coupled to the tip, and a hose connected to the swivel assembly and fluidly coupled to the tip via the swivel assembly. The swivel assembly prevents translation of rotational movement of the handle or the hose relative to the other.

In a further implementation, the swivel assembly further includes a stationary connector keyed to the housing, a swivel connector partially received within the stationary connector and rotatable relative thereto, and a fluid seal positioned between the stationary connector and the swivel connector.

In another implementation, the stationary connector defines a cylindrical receiving cavity and an outlet port. The swivel connector defines a cylindrical disk that rotatably seats within the receiving cavity and an inlet port to which the hose is connected.

In a further implementation, the cyclindrical disk may further include a first disk portion of a first diameter; and a second disk portion of a second diameter larger than the first diameter. The second disk portion seats against an interior wall of the stationary connector. The fluid seal seats around the first disk portion and interfaces with an interior wall of the stationary connector.

In yet another implementation, the handle housing further includes a first ledge and a second ledge each extending normally from an interior wall of the housing and each defining an aperture therethrough. The second ledge is spaced apart from the first ledge along a longitudinal dimension of the housing. A top surface of the stationary connector abuts a bottom surface of the first ledge and the outlet port extends through the aperture in the first ledge. A top surface of the second ledge abuts a bottom surface of the swivel connector and the inlet port extends through the aperture in the second ledge.

In a further implementation, the swivel connector further includes a third disk portion of a third diameter larger than the second diameter to extend as a flange and a bottom surface of the third disk portion abuts the top surface of the second ledge.

In an implementation, an oral irrigator handle is disclosed. The oral irrigator handle may include a housing and a first fitting positioned within the housing that includes a first fitting inlet in fluid communication with a handle inlet in fluid communication with a fluid source, a first fitting outlet in fluid communication with the first fitting inlet. The oral irrigator handle may also include a seal positioned around an outer surface of the first fitting, the seal positioned between the first fitting inlet and the first fitting outlet and a second fitting positioned within the housing. The second fitting may include a second fitting inlet in fluid communication with the first fitting outlet and a second fitting outlet in fluid communication with the second fitting outlet, where a bottom portion of the second fitting is configured to seat on a portion of the first fitting such that the seal engages an interior surface of the second fitting. The handle may also include a flow passage coupled to the second fitting and in fluid communication with the second fitting outlet and a nozzle coupled to the housing, where the nozzle is fluidly coupled to the flow passage.

In another implementation, a handle for an oral irrigating device is disclosed. The handle may include a housing, a nozzle releasably coupled to the housing, a bottom body configured to couple to a hose, including a first disk and a second disk operably coupled to the first disk, where the second disk has a diameter that is smaller than a diameter of the first disk, a seal received around the second disk, and a top body positioned between the nozzle and the bottom body. The top body may include an outer wall defining a reception cavity therein and a top body outlet in fluid communication with the nozzle, where the reception cavity is configured to receive the second disk of the bottom body therein such that the seal engages an interior surface of the outer wall.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

The present disclosure is generally related to a swivel assembly for a handle for an oral irrigator. The swivel assembly allows the hose to rotate 360 degrees relative to the handle such that, as a user moves the handle in various directions and/or rotates the handle, the hose can spin within the handle, reducing the chance that the hose will become tangled, bent, or the like. In other words, the swivel assembly prevents rotational movement of either the handle or the hose from being transmitted to the other, such that rotation of the handle does not affect the position of the hose. The swivel assembly can be positioned within the handle housing or outside the housing (e.g., beneath the handle) to allow the relative motion of the hose to the handle.

Figure 1:
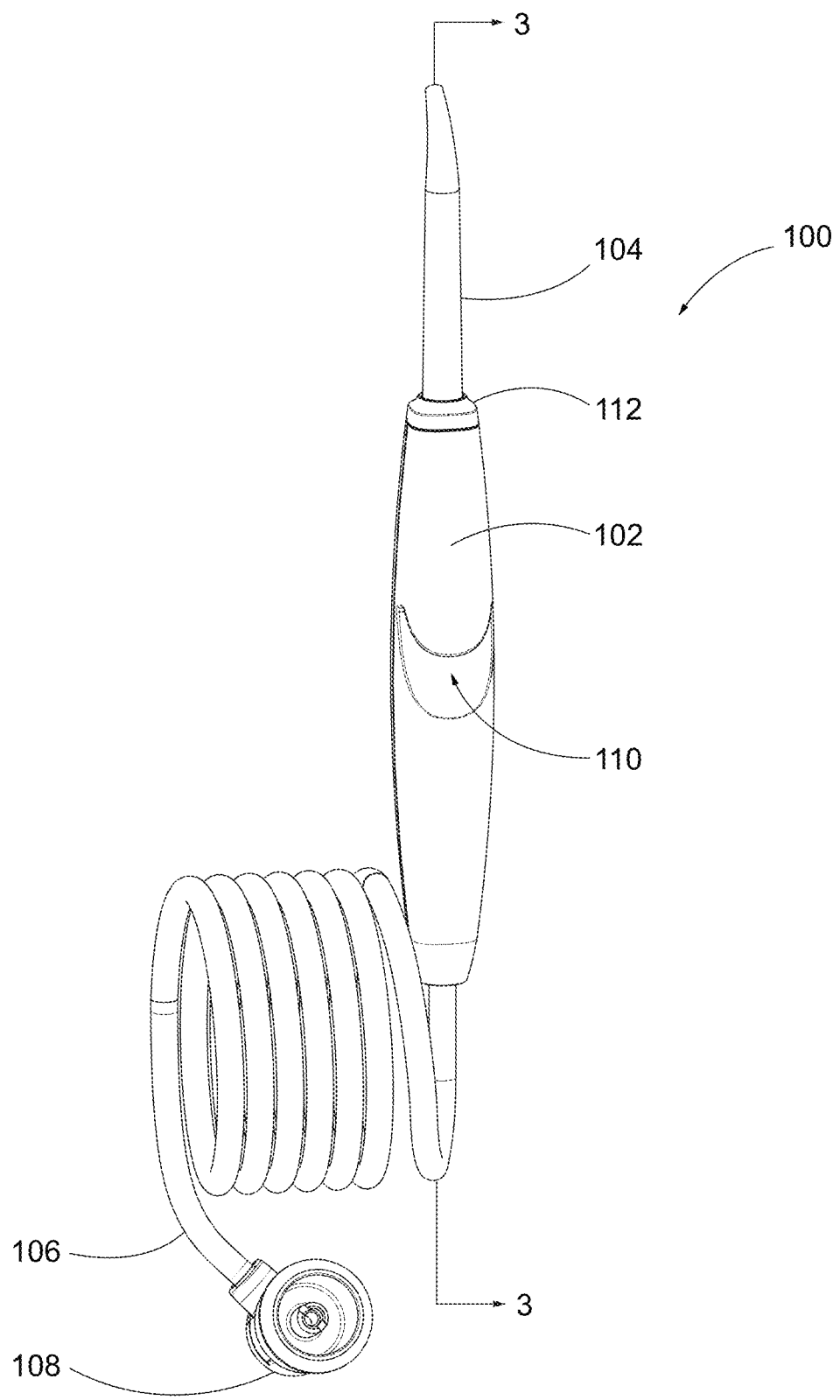
FIG. 1 is a rear elevation view of a handle for an oral irrigator connected to a hose for a base unit.
Figure 2:
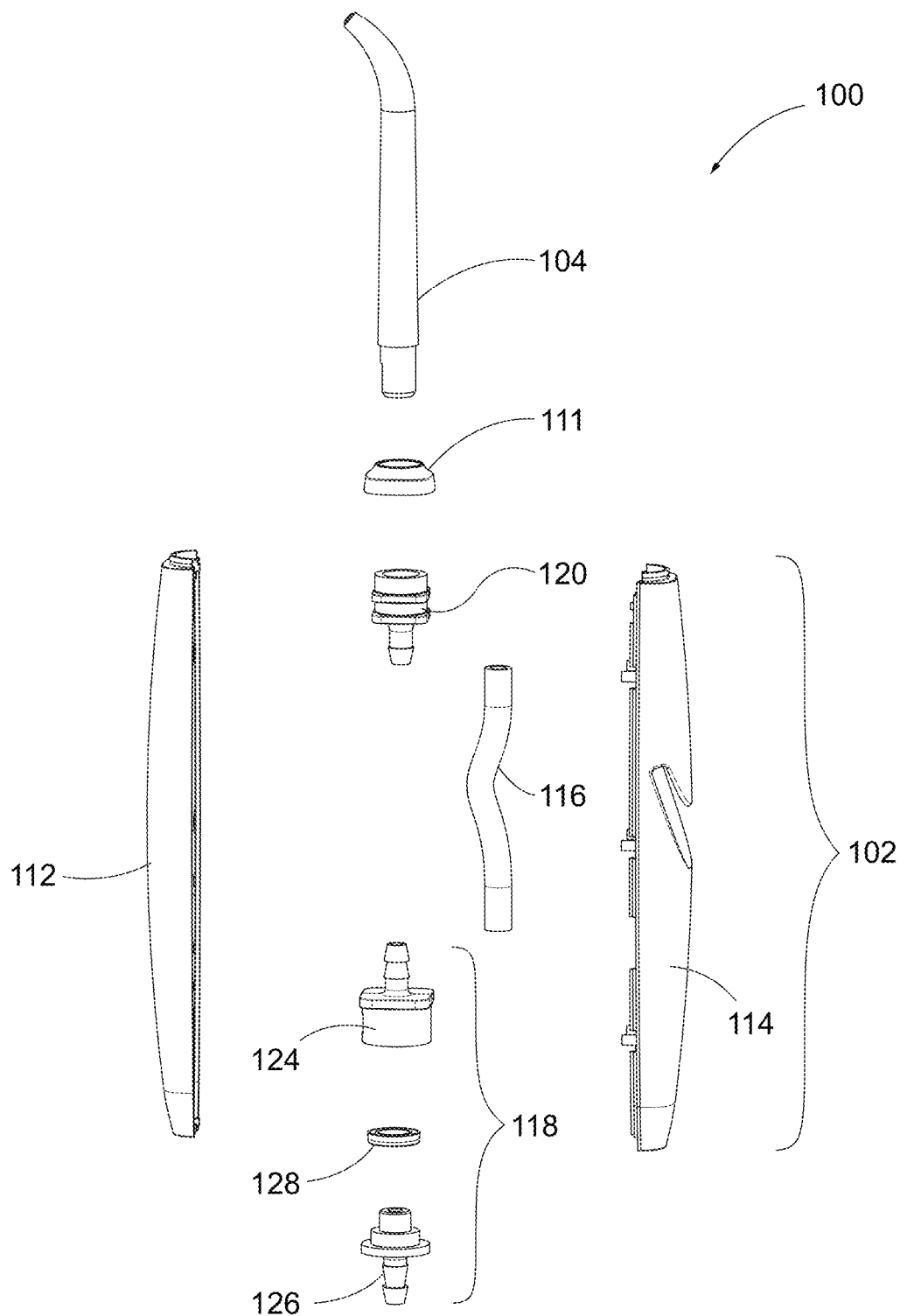
FIG. 2 is an exploded view of the handle of FIG. 1.

With reference to FIGS. 1 and 2, the handle 100 includes a main body or housing 102 and a tip 104 connected to the housing 102. A hose 106 connects the handle 100 to a fluid source, and optionally may include a connector 108 for connecting the hose 106 to the fluid source (e.g., connecting the hose 106 to a base unit). A swivel assembly 118 is connected to the housing 102 and the hose 106 and allows the hose 106 and the housing 102 to rotate relative to one another.

Figure 3:
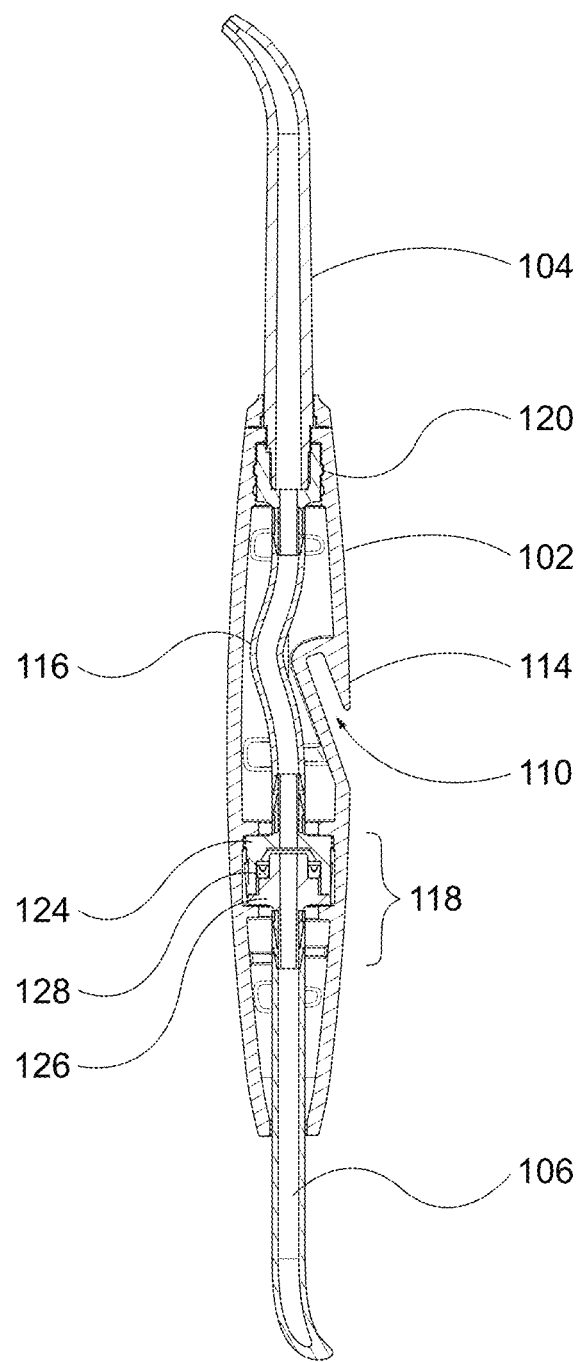
FIG. 3 is a cross-section view of the handle of FIG. 1 taken along line 3-3 in FIG. 1.
Figure 12:
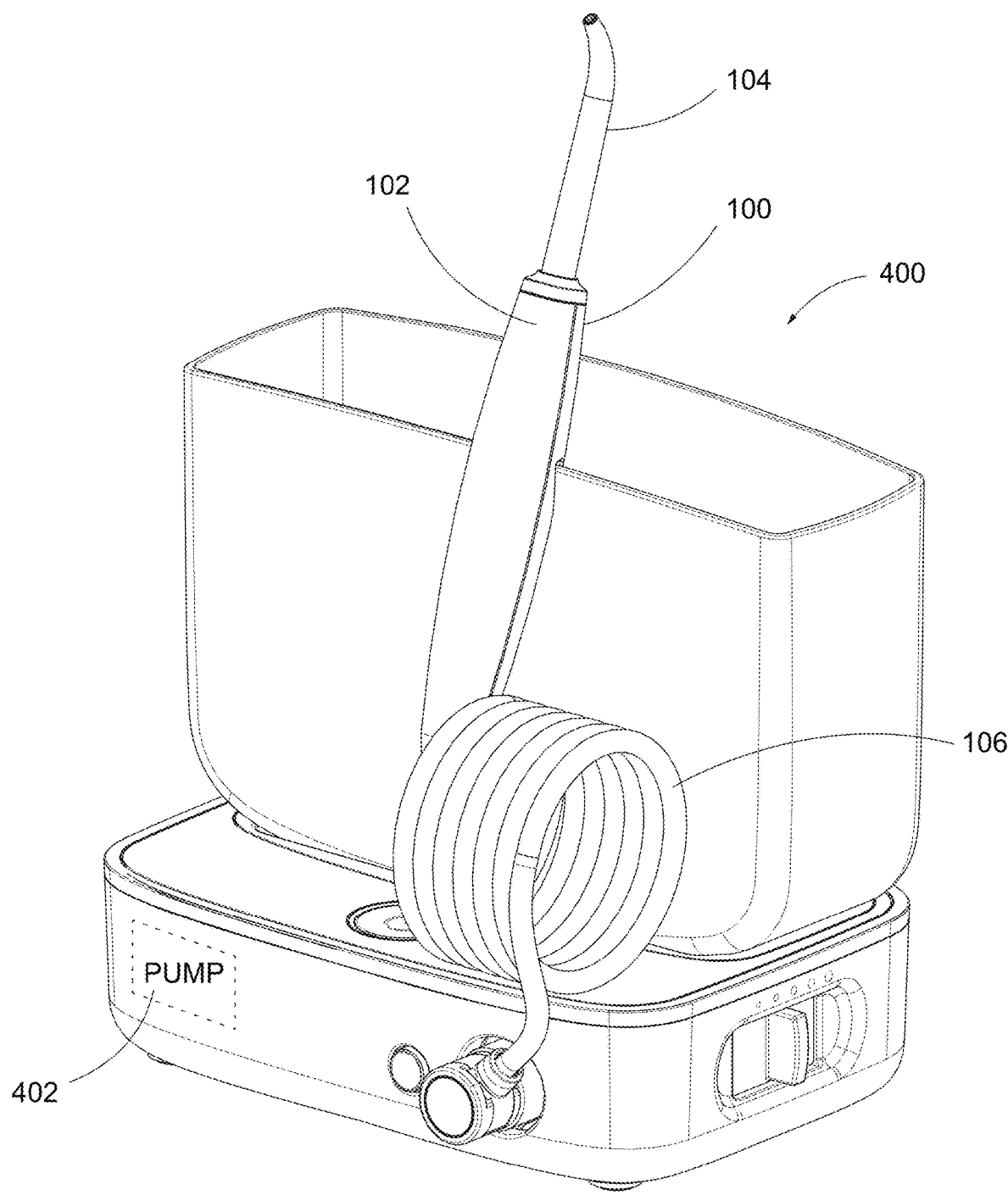
FIG. 12 is a perspective view of an oral irrigator including the handle of FIG. 1.

The housing 102 forms a main body for the handle 100 and can be configured to be easily grasped by the hand of a user. In these embodiments, the housing 102 may form a generally elongated tube. Additionally, the housing 102 may be configured to connect to a storage component of an oral irrigator base, such as a C-clamp, cutout, or the like. In one embodiment, the housing 102 includes an integrated hanging feature 110. In this embodiment, the hanging feature 110 is defined as an angled groove or slot extending at an angle into the housing 102. FIG. 3 is a cross section of the handle 100. As shown in FIG. 3, the hanging feature 110 is an upwardly angled groove that begins at approximately a mid-section of the housing 102 and is angled at approximately a 45 degree angle toward the tip 104. The angle of the hanging feature 110 can be varied depending on a desired storage angle of the tip relative to the base. (See FIG. 12 illustrating the angle of the handle 100 in the storage position.)

Figure 4A:
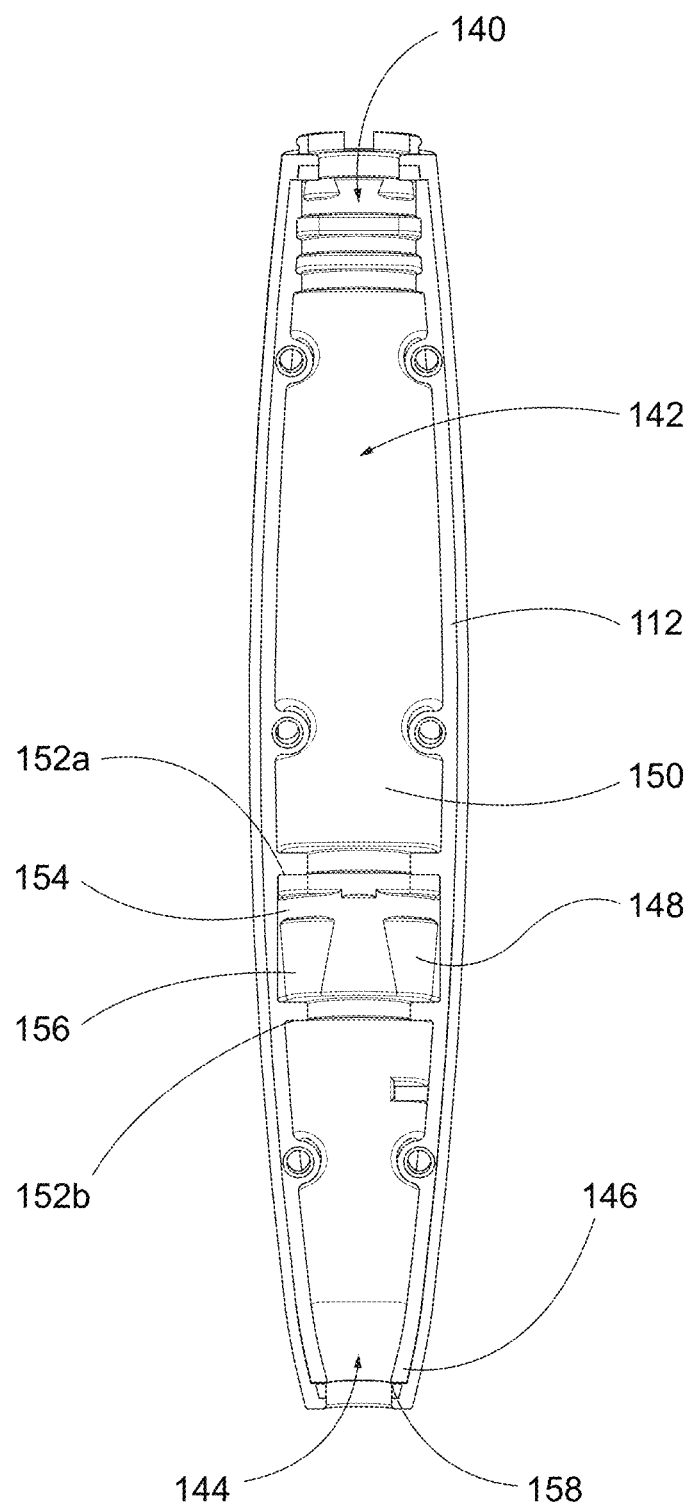
FIG. 4A is a front elevation view of a first shell of a handle housing for the handle of FIG. 1.
Figure 4B:
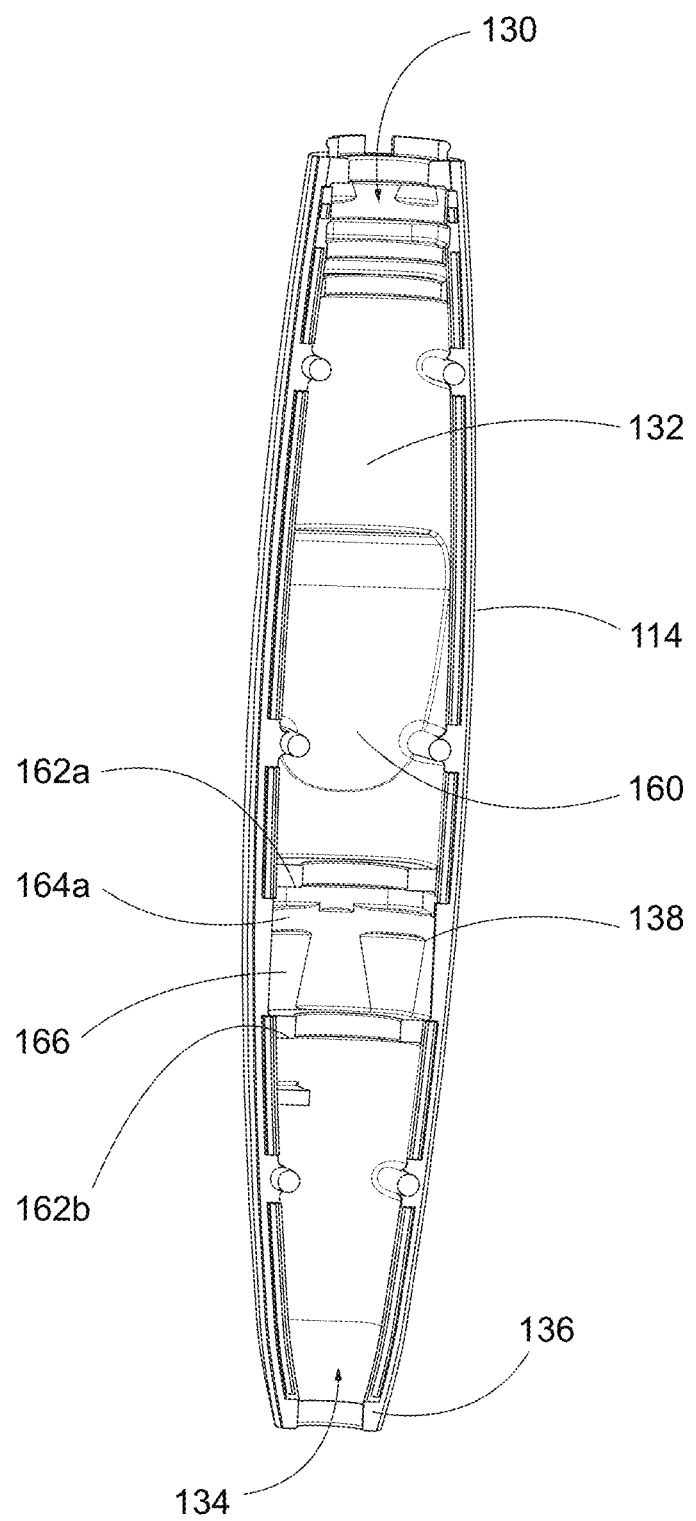
FIG. 4B is a front elevation view of a second shell of the handle housing.

In some embodiments, the housing 102 may be formed as two shells 112, 114 that connect together. FIGS. 4A and 4B illustrate elevation views of the handle shells. With reference to FIG. 4A, a first shell 112 defines a housing cavity 142 that extends laterally along a length of the shell 112. The top end of the first shell 112 includes a cutout defining a tip aperture 140 that extends into the cavity 142. An interior wall 150 of the first shell 112 may include one or more support features 148 defined integrally therewith. The support features 148 are configured to support various components of the swivel assembly 118 and may be modified as desired to support the components. In one embodiment, the support features 148 include upper and lower support ledges 152a, 152b formed as circular steps that extend outward from the interior surface 150 and a groove 154 defined as a slot extending into the interior surface 150 and recessed therefrom. In one embodiment, the groove 154 defines the upper support ledge 152a. In other embodiments, the upper support ledge 152a may be defined in other manners. One or more angled features 156 may be formed between the ledges 152a, 152b as frustum-shaped or tapered slots that extend into the interior surface 150. The angled features 156 may be configured to receive components of the swivel assembly 118, as well as reduce the weight of the housing 102.

A bottom end of the first shell 112 tapers toward the terminal end. The interior surface 150 angles inward to form a tapered wall 146 having an initial taper that flares out at an inflection point 158 to form the hose aperture 144.

With reference to FIG. 4B, the second shell 114 may be substantially a mirror image of the first shell 112 and configured to mate therewith. In one embodiment, however, the second shell 114 includes the hanging feature 110 and thus an upper portion of the interior surface 160 forms an angled wall. The ledges 162a, 162b, the groove 162, the angled features 166, the tapered wall 136, and the hose aperture 134 are substantially the same as those in the first shell 112.

Figure 5:
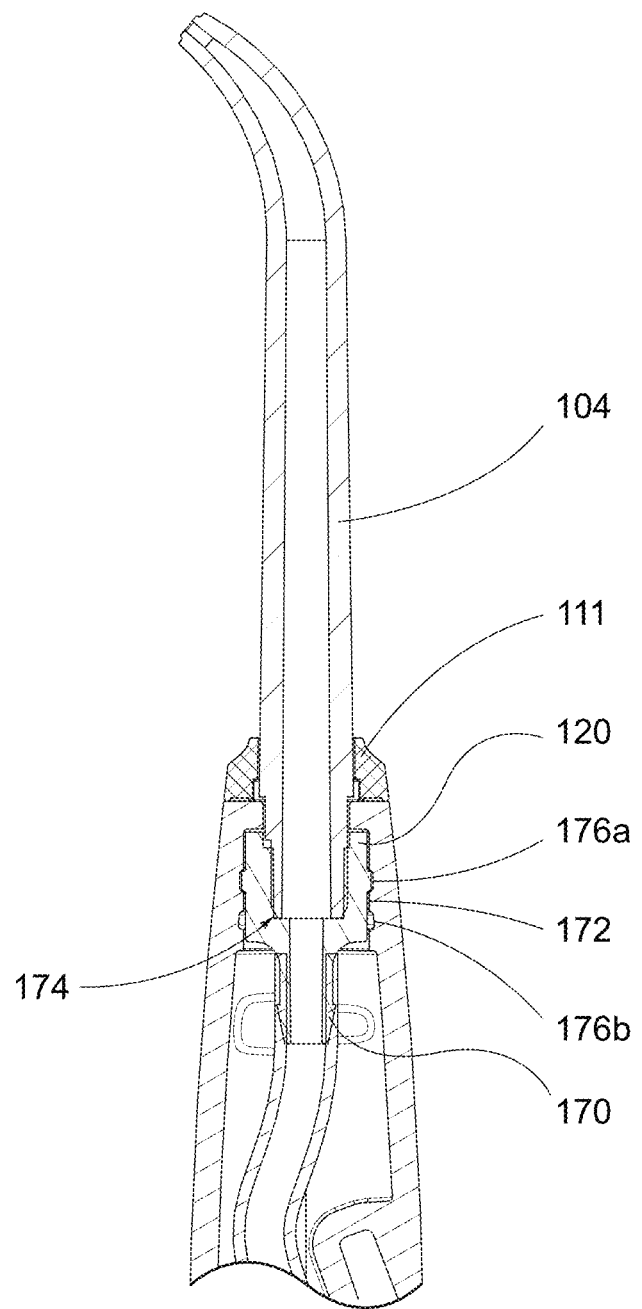
FIG. 5 is an enlarged view of FIG. 3 illustrating a tip connector of the handle.
Figure 6:
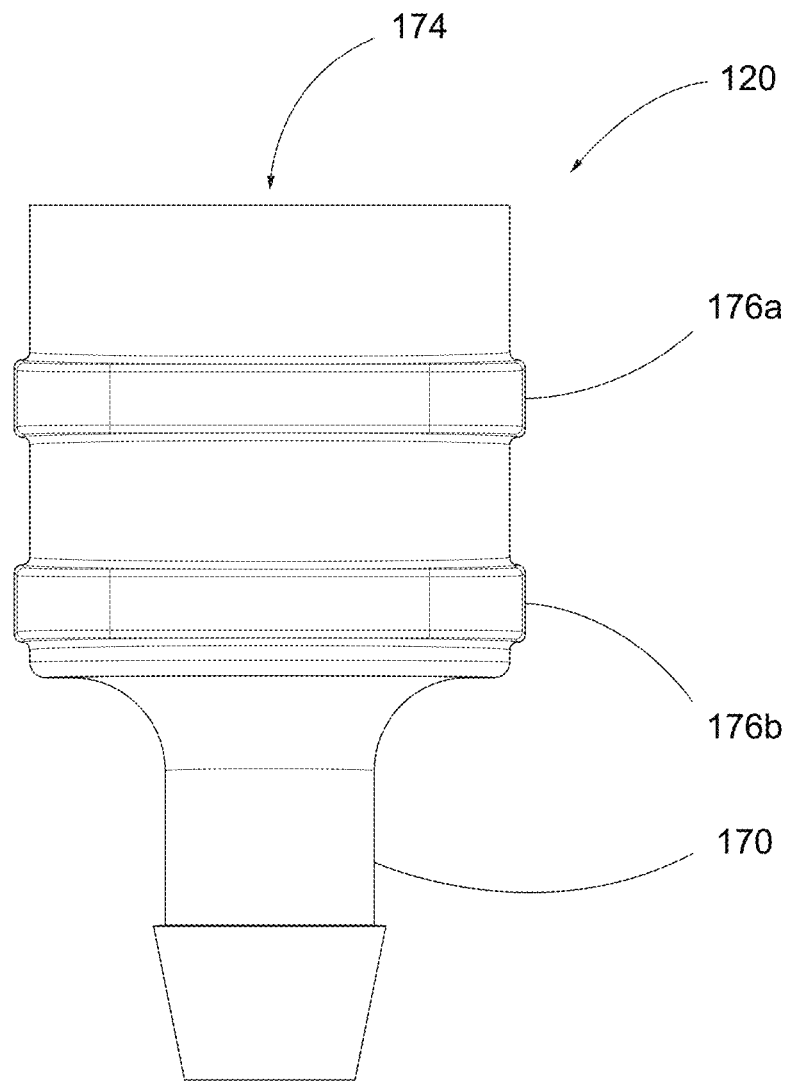
FIG. 6 is a front elevation view of a tip fitting for the handle of FIG. 1.

The handle 100 may also include a tip fitting 120 for securing the tip 104 to the housing 102. FIG. 5 is an enlarged view of the cross-section view of FIG. 3. FIG. 6 is a front elevation view of the tip fitting 120. With reference to FIGS. 5 and 6, the tip fitting 120 includes a main body 172 with a barb 170 extending downward therefrom. The main body 172 may be a hollow member, such as a cylindrical tube that defines an interior cavity 174 sized to receive the bottom end of the tip 104. The barb 170 is also hollow defining a fluid path that extends from the interior cavity 174 through the barb 170. In use, the barb 170 acts as an inlet into the interior cavity 174 such that when the tip 104 is positioned within the cavity 174, the barb 170 is in fluid communication therewith.

The tip fitting 120 may also include alignment flanges 176a, 176b that extend from the outer surface of the main body 172. In one embodiment, the alignment flanges 176a, 176b are defined as substantially rectangular protrusions with curved corners. The alignment flanges 176a, 176b engage with of the housing 102 and fit between ribs in the interior surfaces 150, 160 to secure the fitting 120 in position within the housing 102.

Figure 7:
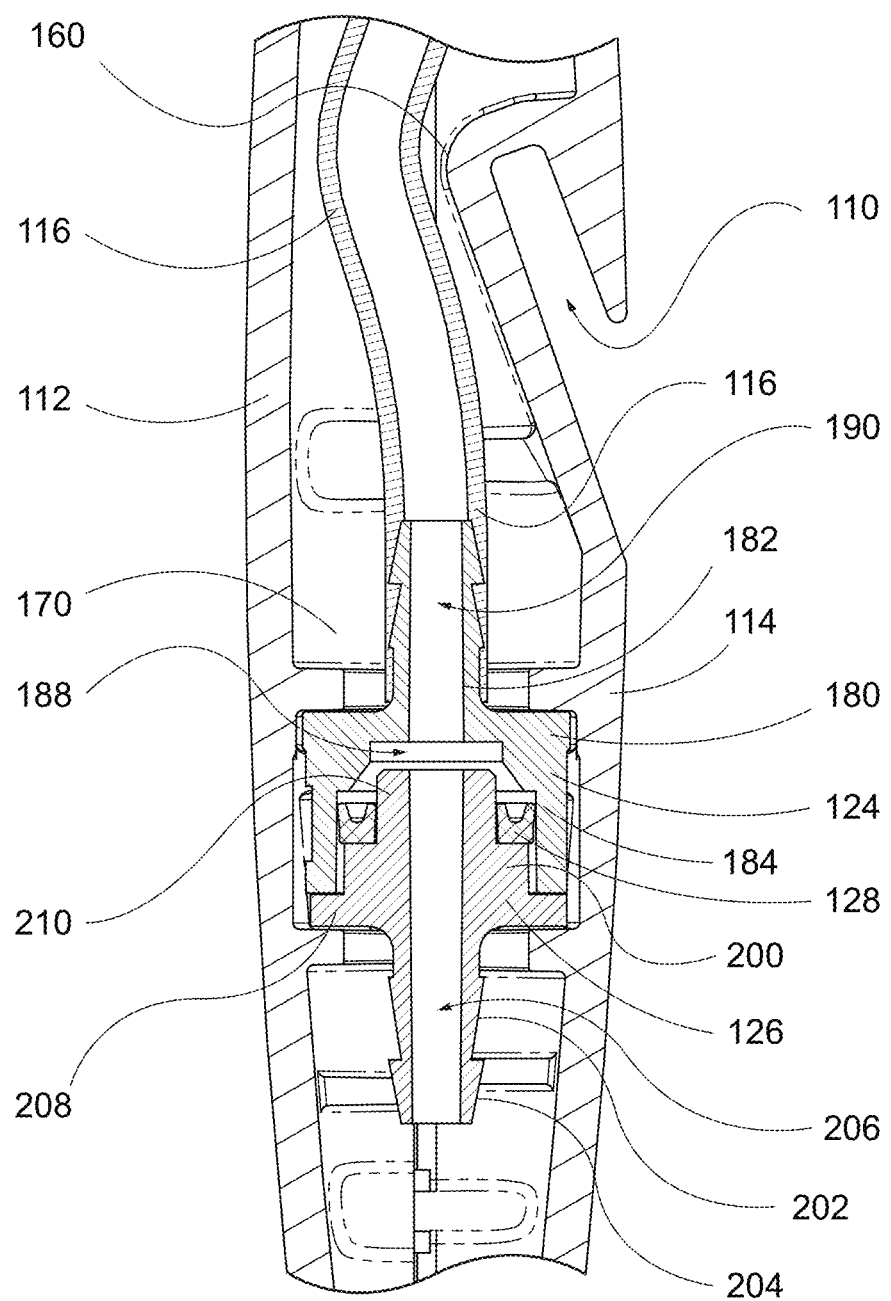
FIG. 7 is an enlarged view of FIG. 3 illustrating a swivel assembly of the handle.

FIG. 7 is an enlarged view of FIG. 3 illustrating the swivel assembly 118. With reference to FIGS. 2, 3, and 7, the swivel assembly 118 includes a stationary connector 124, a swivel connector 126, and a sealing element 128. Each of the components is discussed in turn, below.

Figure 8:
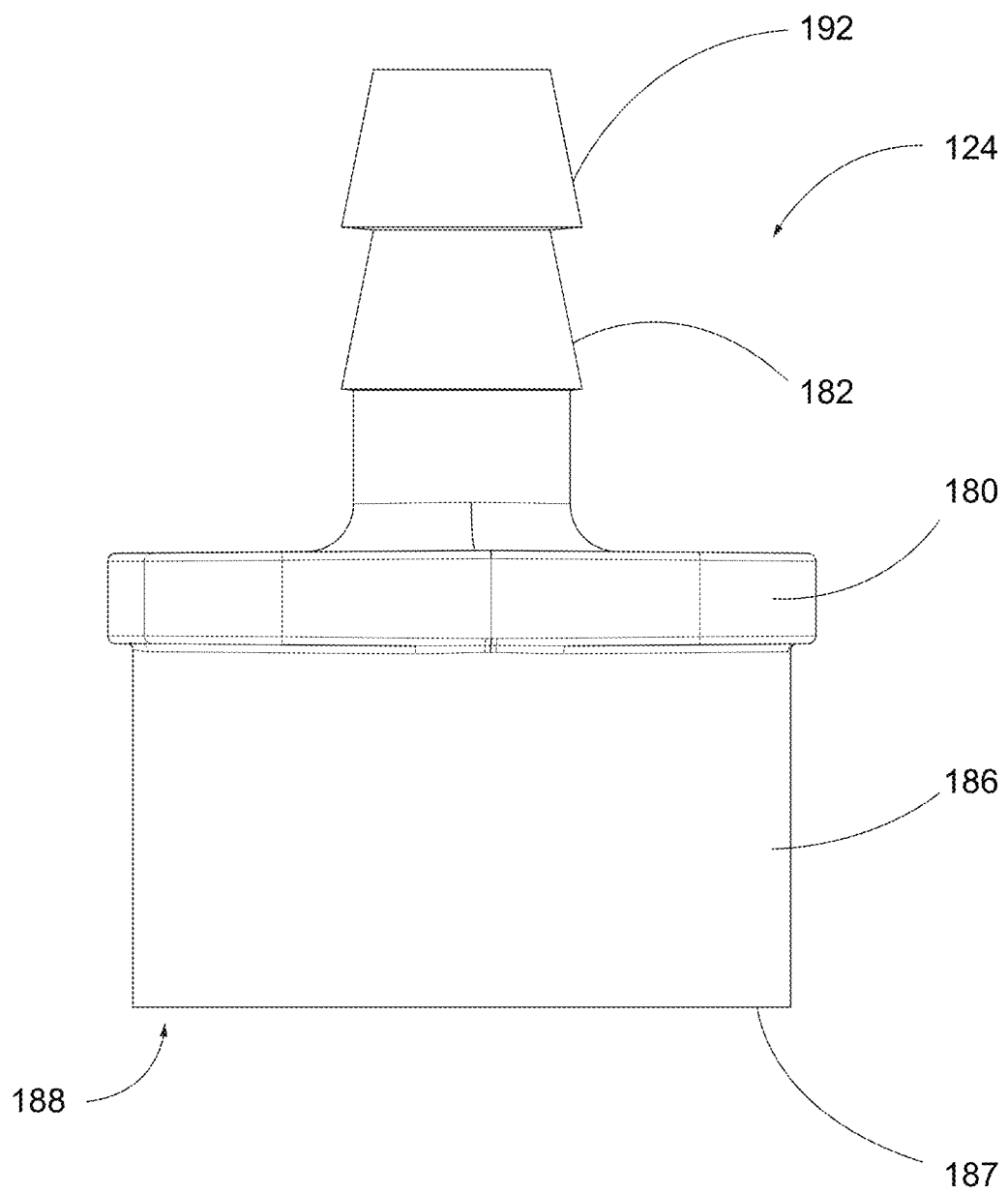
FIG. 8 is a front elevation view of a stationary connector of the swivel assembly.

The stationary connector 124 fluidly connects the swivel assembly 118 to the tube 116 and tip 104. The stationary connector 124 is configured to engage the interior surfaces 150, 160 of the housing 102 to remain stationary relative thereto. FIG. 8 is a front elevation view of the stationary connector 124. With reference to FIGS. 7 and 8, the stationary connector 124 includes a reception cavity 188 defined by an outer wall 186. A securing feature 180 extends from the top end of the outer wall 186. In one embodiment, the outer wall 186 is substantially cylindrical and the securing feature 180 is substantially rectangular or square shaped and the securing feature 180 extends past the outer perimeter of the outer wall 186 to define a lip for the stationary connector 124.

A connection barb 182 extends from the top surface of the securing feature 180. The connection barb 182 may include one or more gripping elements 192 to enhance the connection of the tube 116 to the barb 182. The barb 182 defines a fluid channel 190 therethrough in fluid communication with the reception cavity 188 and acts as an outlet port for fluid flowing through the reception cavity 188. The fluid channel 190 is in fluid communication with the reception cavity 188 defined by the outer wall 186.

The stationary connector 124 may also include one or more component ledges 184 or steps defined on an interior surface of the outer wall 186. The component ledges 184 are used to seat components such as the sealing member 128 or the like.

Figure 9:
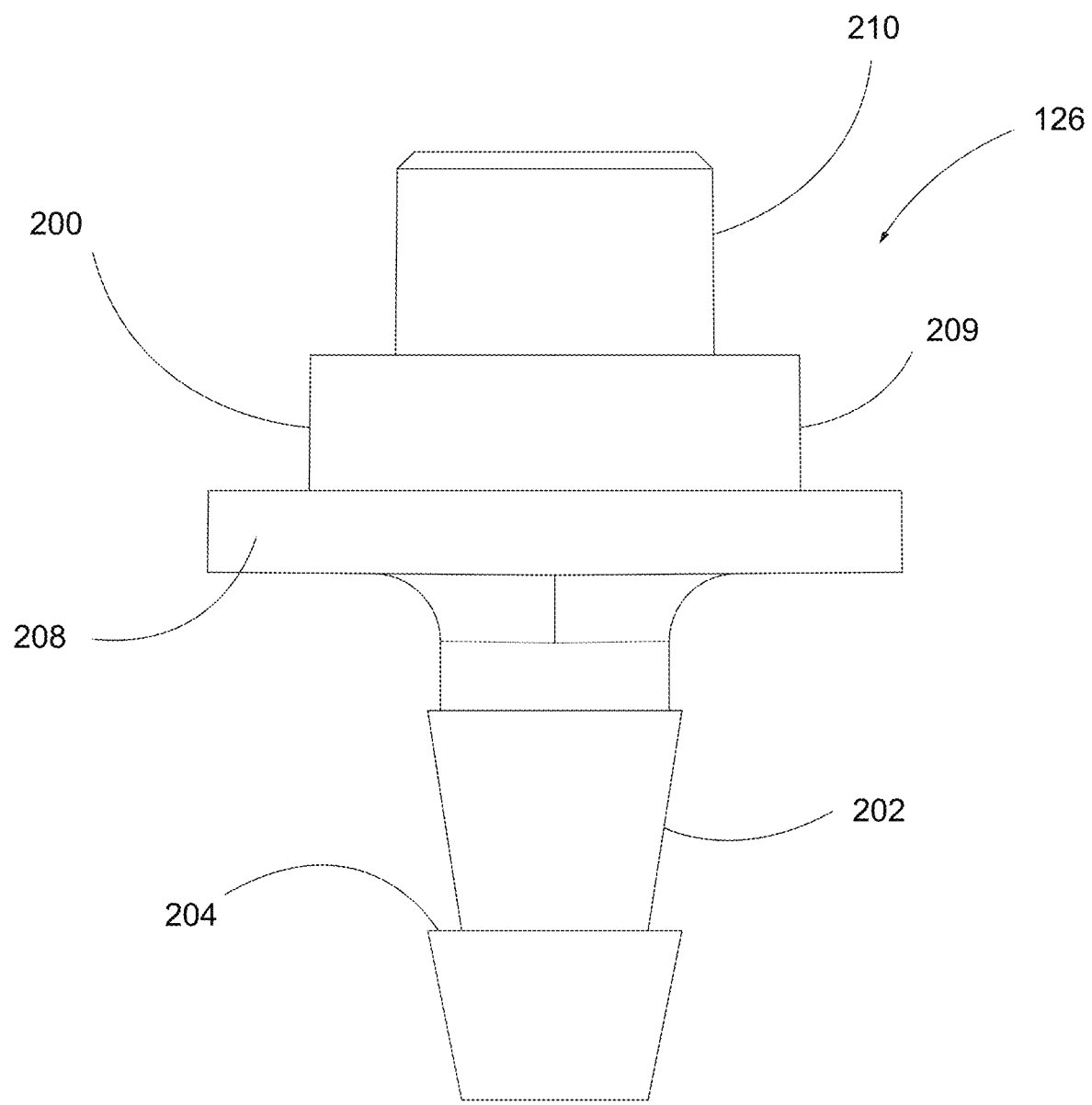
FIG. 9 is a front elevation view of a swivel connector of the swivel assembly.

With reference again to FIG. 7, the swivel connector 126 is configured to be received within and rotate relative to the stationary connector 124. In this manner, the swivel connector 126 does not translate rotational movement to the handle, since it can rotate relative to the handle. FIG. 9 is a front elevation view of the swivel connector 126. With reference to FIGS. 7 and 9, the swivel connector 126 defines a flow passage 206 that extends along the entire longitudinal length of the swivel connector 126. A bottom end of the swivel connector 126 includes a barb 202 that defines a portion of the flow passage 206 and has one or more gripping components 204 that enhance the connection between the swivel connector 126 and the hose 106. The barb 202 acts as an inlet port for fluid flow through the handle 100 from the hose 106.

In one embodiment, the main body 200 of the swivel connector 126 may be formed as a series of stacked concentric disks. For example, the top disk 210 has the smallest radius of the stack and the middle disk 209 has a diameter between those of the top disk 210 and the bottom disk 208. The axial length or thickness of each of the disks 208, 209, 210 increases between each disk, with the bottom disk 208 having the shortest thickness, the middle disk 209 having a thickness between the top and bottom disks 208, 210, and the top disk 210 having the largest thickness. As should be appreciated, the configuration of the main body 200, and specifically the disks 208, 209, 210, is variable based on the configuration of the stationary connector 124.

With reference to FIGS. 2 and 3, the handle 100 may include a tube 116 for fluidly connecting the swivel assembly 118 to the tip fitting 120. The tube 116 in some embodiments is flexible and configured to bend around the interior surface 160 of the shell 114 forming the hanging feature 110.

The assembly of the handle 100 will now be discussed with reference to FIGS. 2, 3, 5, and 7. The tip fitting 120 is inserted into a top end of one of the shells 112, 114 and the jet tip 104 is inserted into the interior cavity 174 of the main body 172. The flow path of the jet tip 104 is aligned with and fluidly connected to the flow path defined through the barb 107. A first end of the tube 116 is connected to barb 170 and the second end of the tube 116 is received around the barb 182 of the stationary connector 124.

With reference to FIGS. 4A, 4B, and 7, the stationary connector 124 is inserted into one of the shells 112, 114. For example, the stationary connector 124 may be first inserted into the first shell 112 with the securing feature 180 received in the groove 154 beneath the first ledge 152a. The sealing member 128, which may be a seal cup, O-ring, or other sealing element, may be positioned around the top disk 210 of the swivel connector 126 and then the top disk 210 of the swivel connector 126 is inserted into the reception cavity 188 of the stationary fitting 124. In this embodiment, the middle disk 208 engages with one of the steps within the outer wall 186 of the stationary connector 124 and the bottom disk 208 extends beneath and engages the bottom edge 187 of the stationary connector 124. The bottom disk 208 of the swivel connector 126 seats on the top surface of the bottom ledge 152b of the shell 112. The top end of the hose 106 is then received around the barb 202 of the swivel connector 126, fluidly connecting the hose 106, the swivel connector 126, the stationary fitting 124, and the tube 116 together.

With the internal components connected together, the opposite shell 112, 114, e.g., the second shell 114 is connected to the first shell 112. The ledges 162a, 162b are aligned with the swivel assembly 118 such that they bookend the securing feature 180 of the stationary connector 124 and the bottom disk 208 of the swivel connector 126. In other words, once the shells are connected together the ledges 152a, 152b, 162a, 162b of the two shells 112, 114 clamp around the swivel assembly 118 to prevent longitudinal movement of the assembly, the stationary connector, or the swivel connector relative to the housing 102. The shells 112, 114 are then secured together, e.g., by ultrasonic welding, with adhesive, press fit, fasteners, or the like. The tip collar 111 may be connected around the outer surface of the tip 104 and seat on the top end of the housing 102 of the handle 104.

In some embodiments, once the tip 104 is connected to the housing 102, the tip 104 may not rotate relative thereto or be ejectable relative thereto. For example, the alignment features 176a, 176b of the tip fitting 120 may key to ribs on the interior surfaces 150, 160 of the housing 102 to prevent rotation and the tip 104, which is press fit into the fitting 120 may be secured correspondingly. However, in other embodiments, conventional tip fitting components and/or eject mechanisms may be used to allow the tip 104 to rotate relative to the housing 102 and allow the tip 104 to be removed from the housing 102.

With reference to FIG. 12, fluids, such as water, that are pumped by a pump 402 from a countertop oral irrigator unit 400 flow through the hose 106, into the fluid passage 206 within the swivel connector 126, into the reception cavity 188 of the stationary connector 124, into the fluid passage 190 within the barb 182 and into the tube 116. From the tube 116, fluid flows into the fluid passage in the barb 170 of the tip fitting 120 and into the tip 104 which is received therein.

During use, as the user moves the handle 100 into different angles and positions to access different areas of his or her mouth, the hose 106 can rotate freely relative to the handle to maintain a desired orientation and be free from tangles and undesired bends or creases. In particular, during use, as the user moves the handle 100 to different orientations, the hose 106, which typically is anchored to a base unit, can rotate at its connection to the handle as the swivel connector 126 rotates within and relative to the stationary connector 124. In these embodiments, the materials of the stationary connector 124 and the swivel connector 126 are selected to be low-friction so as to introduce minimal to no drag.

Alternative Embodiment

Figure 10:
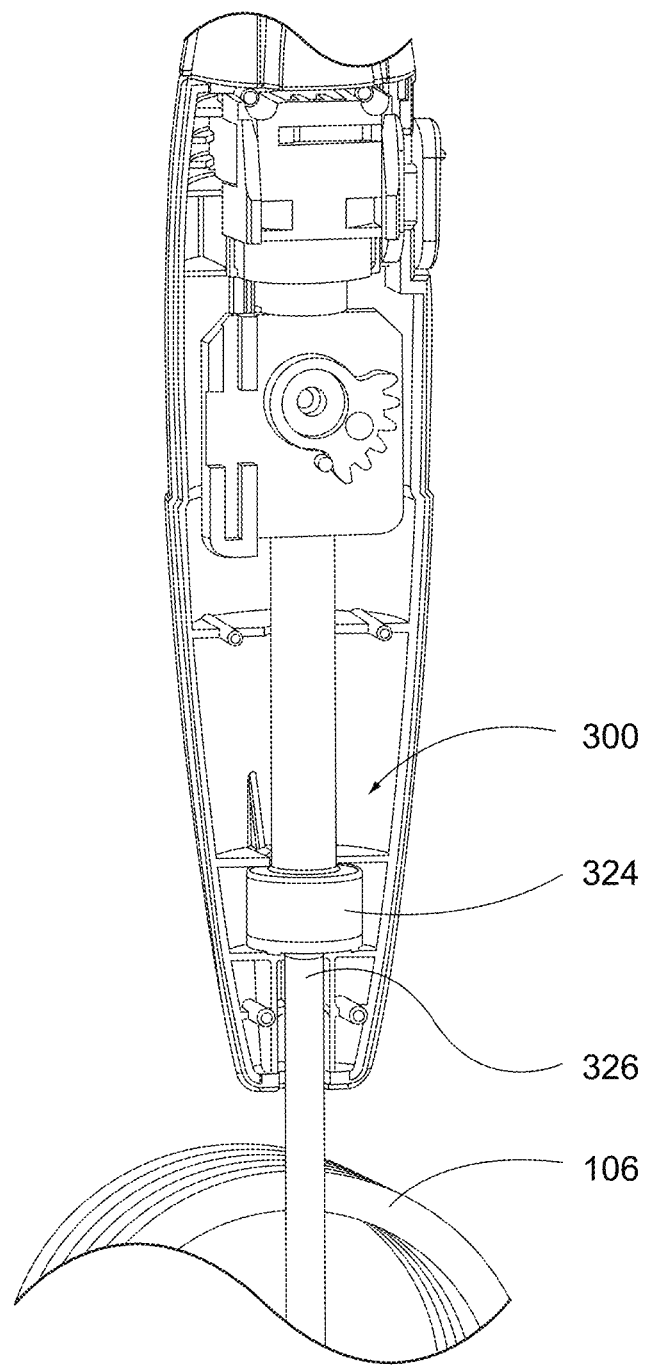
FIG. 10 is a front elevation view of another example of a handle with the swivel assembly with a first shell of the handle hidden to illustrate the internal components.
Figure 11:
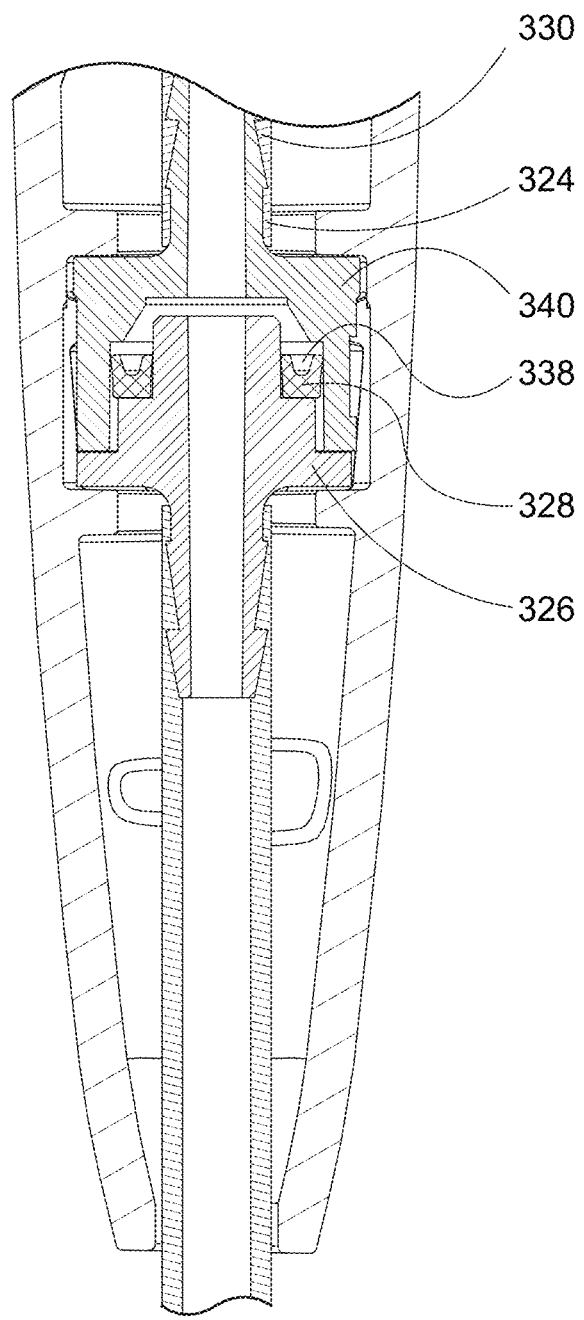
FIG. 11 is an enlarged cross-section view of the handle of FIG. 10 taken along a line similar to line 3-3 in FIG. 1.

In some embodiments, the tube 116 and the stationary connector 124 may be integrally formed. FIGS. 10 and 11 illustrate views of another embodiment of the handle 100. With reference to FIGS. 10 and 11, in this embodiment, the swivel assembly 300 includes a stationary connector 324, a swivel connector 326, and a sealing member 328, each of which may be substantially the same as the corresponding components in the swivel assembly 118. However, in this embodiment, the stationary connector 324 includes an extended tube 330 rather than a barb at its top end. The tube 330 is formed integrally with the main body of the connector 324 and is fluidly connected the reception cavity 338 formed by the outer wall 340.

In these embodiments, the tube 330 may connect directly to a tip fitting to fluidly connect to the tip 104. Additionally, as mentioned above, in this embodiment, the handle may include a pause switch assembly and tip ejection assembly. Examples of these assemblies are described in U.S. patent application Ser. No. 14/555,339 filed on 26 Nov. 2014 entitled "Oral Irrigator with Slide Pause Switch," which is hereby incorporated by reference herein in its entirety.

All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An oral irrigator handle comprising:
   a housing;
   a first fitting positioned entirely within the housing, the first fitting comprising:
      a first fitting inlet in fluid communication with a handle inlet in fluid communication with a fluid source; and
      a first fitting outlet in fluid communication with the first fitting inlet;
   a seal positioned around an outer surface of the first fitting, the seal positioned between the first fitting inlet and the first fitting outlet;
   a second fitting positioned entirely within the housing, the second fitting comprising:
      a second fitting inlet in fluid communication with the first fitting outlet; and
      a second fitting outlet in fluid communication with the second fitting inlet; wherein
      a bottom portion of the second fitting is configured to seat on a portion of the first fitting such that the seal engages an interior surface of the second fitting;
   a flow passage coupled to the second fitting and in fluid communication with the second fitting outlet; and
   a nozzle coupled to the housing, wherein the nozzle is fluidly coupled to the flow passage.

2. The oral irrigator handle of claim 1, wherein the first fitting further comprises:
   a base portion; and
   a neck operably connected to the base portion and having a reduced diameter as compared to a diameter of the base portion, wherein the seal is received around the neck.

3. The oral irrigator of claim 2, wherein the bottom portion of the second fitting is configured to seat on a top surface of the base portion.

4. The oral irrigator of claim 2, wherein the first fitting further comprises a barb extending from the base portion, wherein the barb defines the first fitting inlet and is configured to couple to a hose coupled to the fluid source.

5. The oral irrigator of claim 2, wherein the base portion is circular shaped.

6. The oral irrigator of claim 1, wherein the second fitting comprises:
   an outer wall defining the bottom portion and a reception cavity configured to receive the first fitting partially therein; and
   a tapered portion extending from the outer wall, wherein the tapered portion defines the second fitting outlet and the reception cavity defines the second fitting inlet.

7. The oral irrigator of claim 1, wherein the housing comprises:
   a first shell; and
   a second shell coupled to the first shell, wherein a housing inlet is defined by an aperture formed by the coupling of the first shell and the second shell.

8. The oral irrigator of claim 7, further comprising a hose mechanically coupled to the first fitting and defining the handle inlet, wherein the hose extends through the housing inlet.

9. The oral irrigator of claim 1, wherein the first fitting comprises at least two stacked disks.

10. The oral irrigator of claim 9, wherein the seal is positioned around a first disk of the at least two stacked disks.

11. The oral irrigator of claim 10, wherein a second disk of the at least two stacked disks defines a base portion of the first fitting, wherein the second fitting is configured to seat at least partially on the base portion.

12. The oral irrigator of claim 1, wherein the housing comprises at least one support ledge that interfaces with the first fitting to prevent axial movement of the first fitting relative to a longitudinal axis of the housing.

13. A handle for an oral irrigating device comprising:
a housing defining an opening in a bottom end of the housing;
a nozzle releasably coupled to the housing;
a bottom body configured to couple to a hose and received entirely within the housing, the bottom body comprising:
  a first disk having a first diameter that is greater than the opening; and
  a second disk operably coupled to the first disk, wherein the second disk has a second diameter that is smaller than the first diameter of the first disk;
a seal received around the second disk; and
a top body positioned between the nozzle and the bottom body and received entirely within the housing, the top body comprising:
  an outer wall defining a reception cavity therein; and
  a top body outlet in fluid communication with the nozzle;
wherein the reception cavity is configured to receive the second disk of the bottom body therein such that seal engages an interior surface of the outer wall.

14. The handle of claim 13, wherein the top body comprises an outlet portion coupled to the outer wall, wherein the outlet portion has a diameter that is less than a diameter of the outer wall.

15. The handle of claim 13, wherein the seal is at least one of a U-cup or an O-ring.

16. The handle of claim 13, wherein a bottom surface of the outer wall of the top body is configured to engage a top surface of the second disk.

17. The handle of claim 13, wherein the housing comprises a support that prevents movement of the bottom body along a longitudinal length of the housing.

18. The handle of claim 13, wherein the bottom body further comprises a barb extending from the second disk, wherein the barb is configured to secure the hose to the bottom body.

19. The handle of claim 13, wherein the bottom body is movable and the top body is fixed relative to the handle.

20. The handle of claim 13, wherein the first disk and the second disk are formed integrally.

* * * * *